United States Patent [19]

Sherman

[11] 4,223,682
[45] Sep. 23, 1980

[54] BEAT-TO-BEAT SYSTOLIC AND DIASTOLIC INDICATOR

[75] Inventor: Allan P. Sherman, Lexington, Mass.

[73] Assignee: Hewlett-Packard Company, Palo Alto, Calif.

[21] Appl. No.: 895,193

[22] Filed: Apr. 10, 1978

[51] Int. Cl.³ .............................................. A61B 5/02
[52] U.S. Cl. ................................. 128/672; 364/417; 324/103 P
[58] Field of Search ..................... 128/2.05 A, 2.05 D, 128/2.05 M, 670–673, 704–706; 324/103 R, 103 P; 364/415–417; 307/351

[56] References Cited

U.S. PATENT DOCUMENTS

| | | | |
|---|---|---|---|
| 2,986,655 | 5/1961 | Wiseman et al. | 324/103 P |
| 3,486,499 | 12/1969 | Yen | 128/672 |
| 3,938,506 | 2/1976 | Birnbaum et al. | 128/2.05 D X |
| 3,939,824 | 2/1976 | Arneson et al. | 128/2.05 A |
| 3,978,848 | 9/1976 | Yen et al. | 128/2.05 M |
| 4,018,219 | 4/1977 | Hojaiban | 128/706 |
| 4,024,459 | 5/1977 | Mears | 324/103 P |
| 4,074,149 | 2/1978 | Naaijer | 324/103 P |
| 4,105,020 | 8/1978 | Matsuoka et al. | 128/2.05 A |
| 4,105,021 | 8/1978 | Williams et al. | 128/2.05 A |

OTHER PUBLICATIONS

Randall, M. J. et al, "Computer Automation of Blood-Pressure Measurements", Proc. of the IEEE, vol. 63, No. 10, Oct. 1975, pp. 1399-1403.

*Primary Examiner*—Robert W. Michell
*Assistant Examiner*—Francis J. Jaworski
*Attorney, Agent, or Firm*—Donald N. Timbie

[57] ABSTRACT

Apparatus and method are disclosed for deriving the maximum and minimum peaks of a wave representing blood pressure by comparing it with offsets that may be arbitrarily set or derived from the blood pressure signal, which offsets are alternatively added to and subtracted from the approximate mean of the blood pressure signal.

14 Claims, 10 Drawing Figures

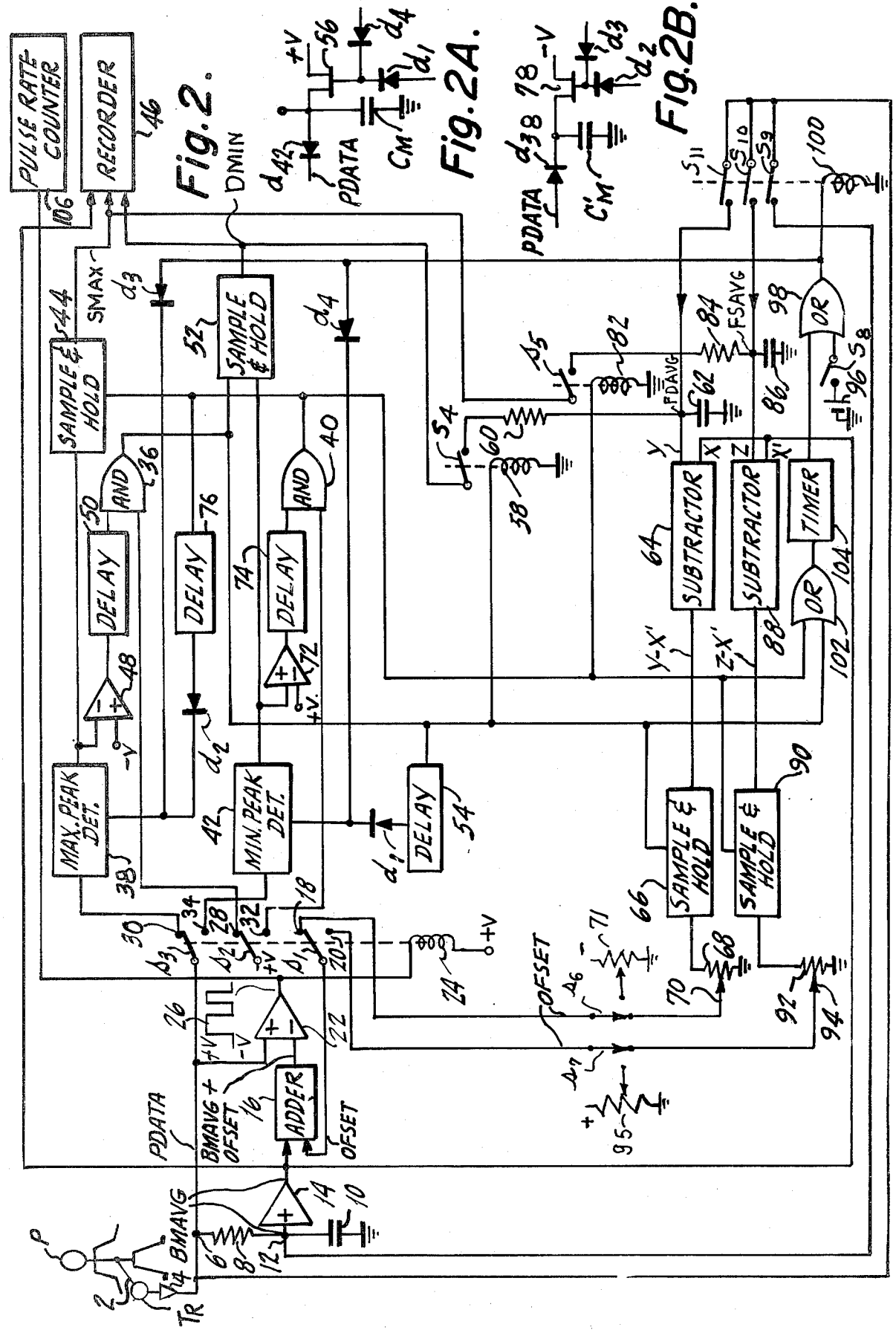

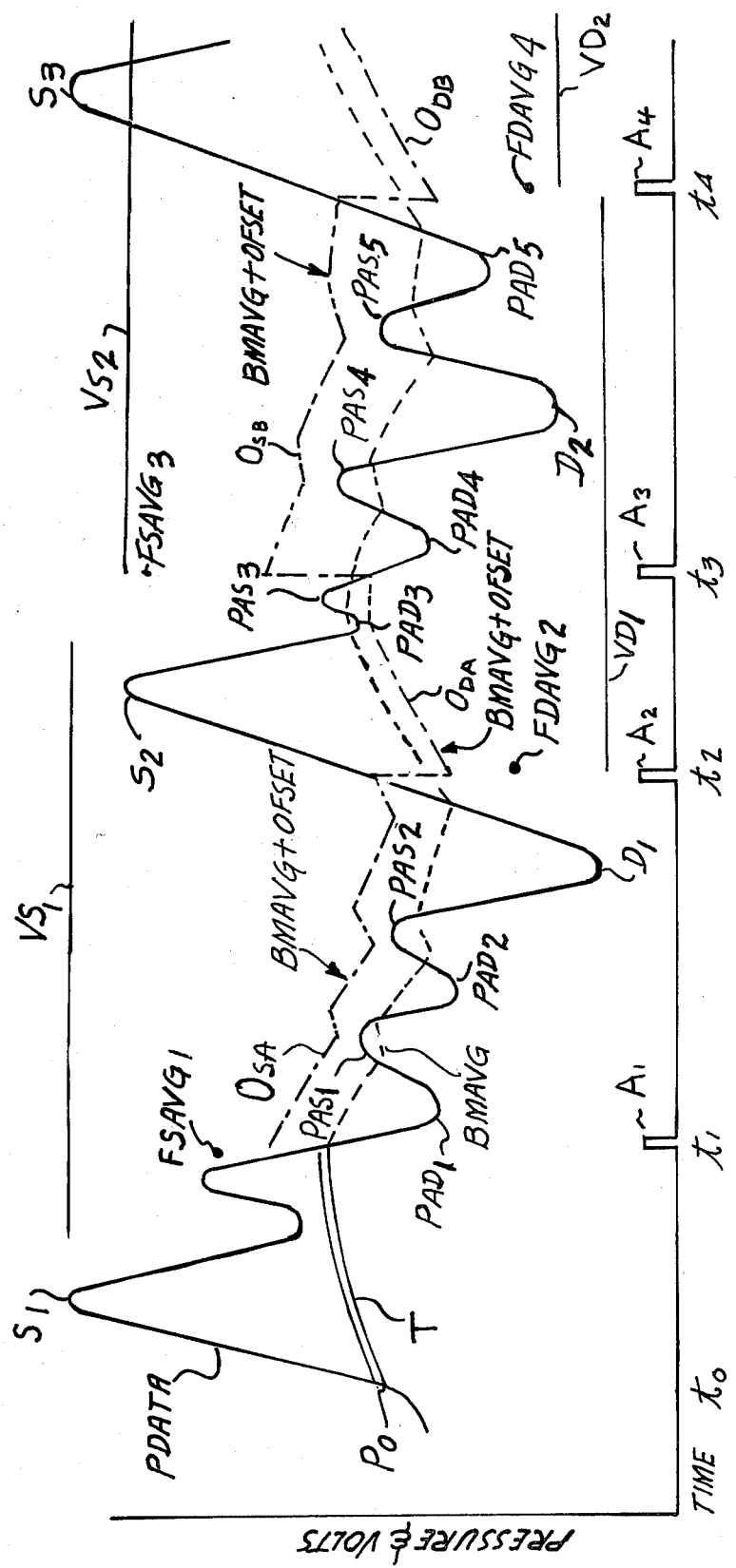

BEAT-TO-BEAT SYSTOLIC AND DIASTOLIC INDICATOR

BACKGROUND OF THE INVENTION

In monitoring the condition of a patient's heart, the systolic and diastolic blood pressures for each heartbeat are measured and recorded. The systolic pressure occurs when the heart contracts so as to cause positive peaks of increased pressure, and the diastolic pressure occurs when the heart relaxes so as to produce negative peaks of decreased pressure. These peaks have been identified in the following way. An ECG machine is coupled to the patient so as to provide at its output electrical signals that vary with the contractions and evaluations of the heart, and a QRS detector is coupled to the output of this ECG machine so as to produce a signal at the same point in each heart cycle. The peaks in the blood pressure signal are identified by correlating their time of occurrence with the signal produced by the QRS detector. Whereas this method works well, it requires signals for both blood pressure and ECG.

BRIEF DISCUSSION OF THE INVENTION

In accordance with one aspect of this invention therefore, the positive and negative peaks of the blood pressure signal that respectively correspond to the systolic and diastolic pressures of each beat are identified directly from the blood pressure signal itself, rather than indirectly through the use of a ECG machine and a QRS detector. A blood pressure signal is derived in any suitable manner such as by inserting a catheter into the appropriate point in the patient's circulatory system and coupling it to a transducer that outputs an electrical signal corresponding to the blood pressure. Means are provided for deriving a signal representing the approximate mean of the blood pressure signal, and other means are provided for comparing the blood pressure signal with its mean. The maximum peak amplitude or systolic pressure is detected during the time the blood pressure signal is greater than its approximate mean, and the minimum peak amplitude or diastolic pressure is detected during the time the blood pressure signal is less than its mean.

This works well as long as the blood pressure signal crosses its mean only once between each true systolic maximum peak and each true diastolic minimum peak, but perturbations which may be due to the properties of the measuring apparatus can cause the blood pressure signal to cross its mean more than once. This causes false peaks to appear between the true systolic and diastolic peaks that are detected along with the true peaks so as to introduce erroneous data.

In accordance with another aspect of this invention, the effect of the false peaks due to perturbations is minimized by subtracting offsets from the mean of the blood pressure signal while the positive systolic peaks are being detected and adding offsets to the mean of the blood pressure signal while the negative diastolic peaks are being detected. The alternating positive and negative offsets to the mean of the blood pressure signal form an offset wave. The peak detecting means operate between the times when the value of the blood pressure signal crosses the value of the offset wave, rather than between the times when it crosses its mean. False peaks due to perturbations will have to have a greater amplitude to cross the values of the offset wave than would be required to cross the value of the mean, so that far fewer false peaks are detected.

THE DRAWINGS

FIG. 2 is a schematic diagram of an analog circuit constructed in accordance with the principles of this invention.

FIG. 2A is a schematic circuit of the minimum peak detector of FIG. 2;

FIG. 2B is a schematic circuit of the maximum peak detector of FIG. 2;

Figure 4:
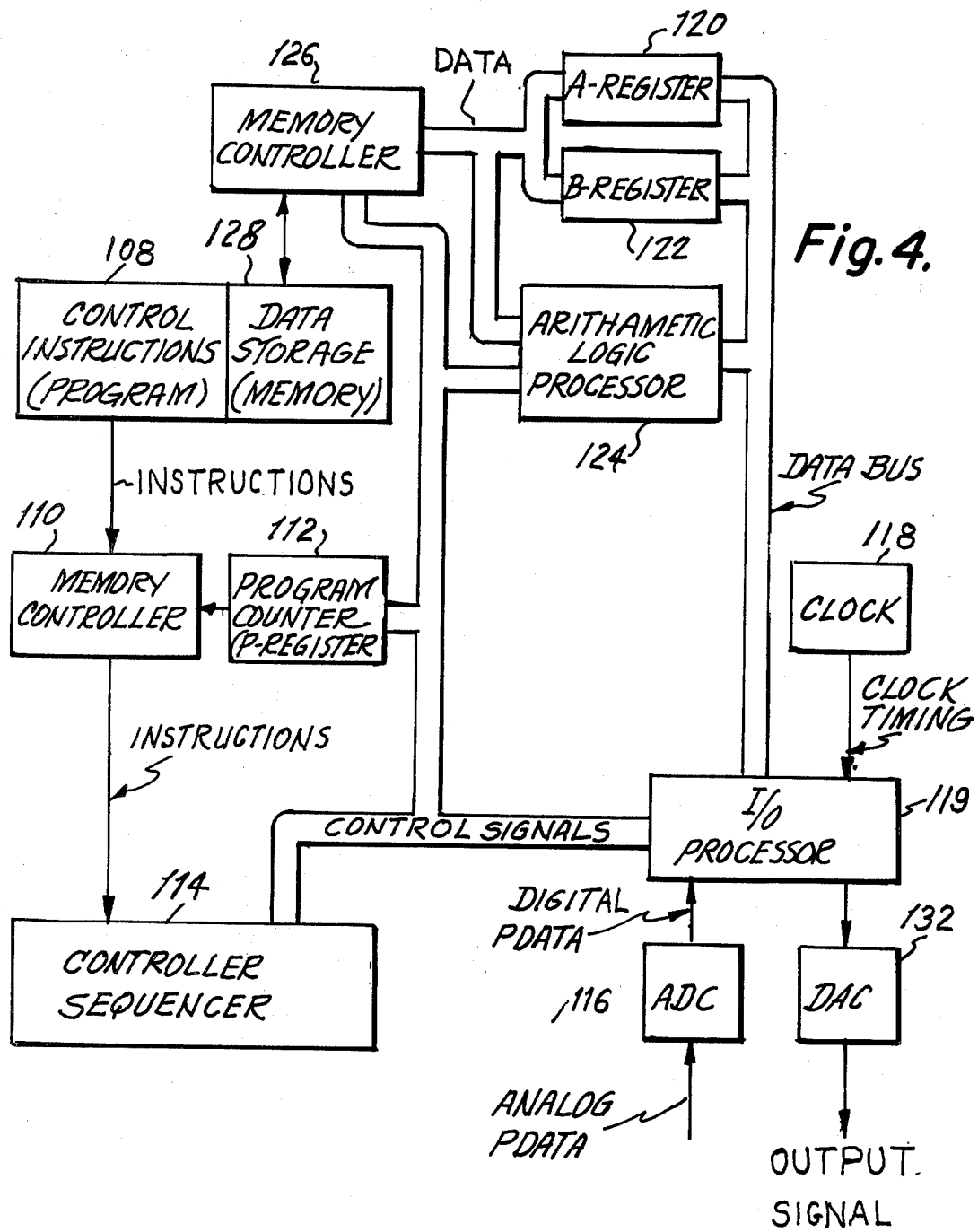
Figure 5A:
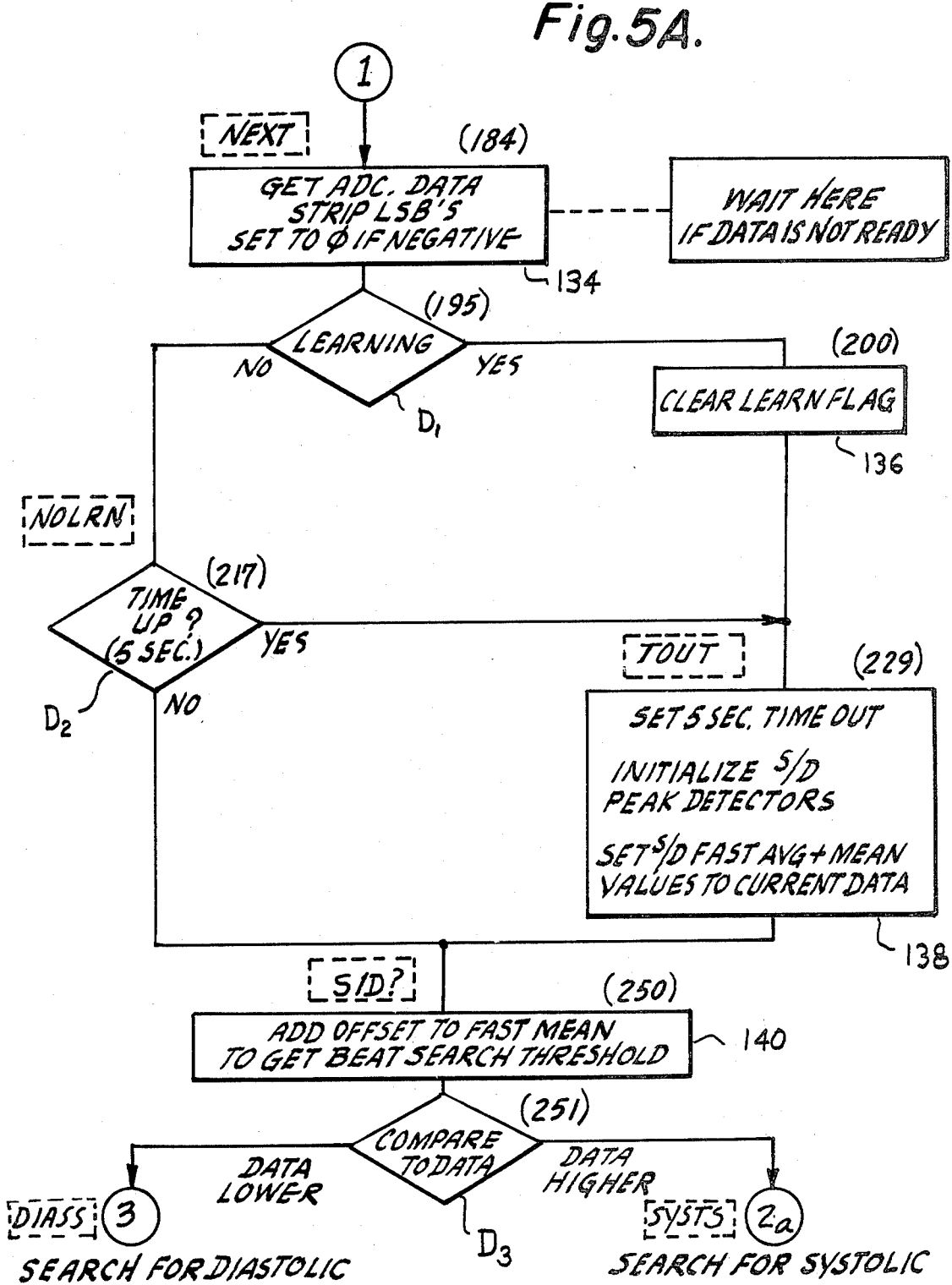
Figure 5B:
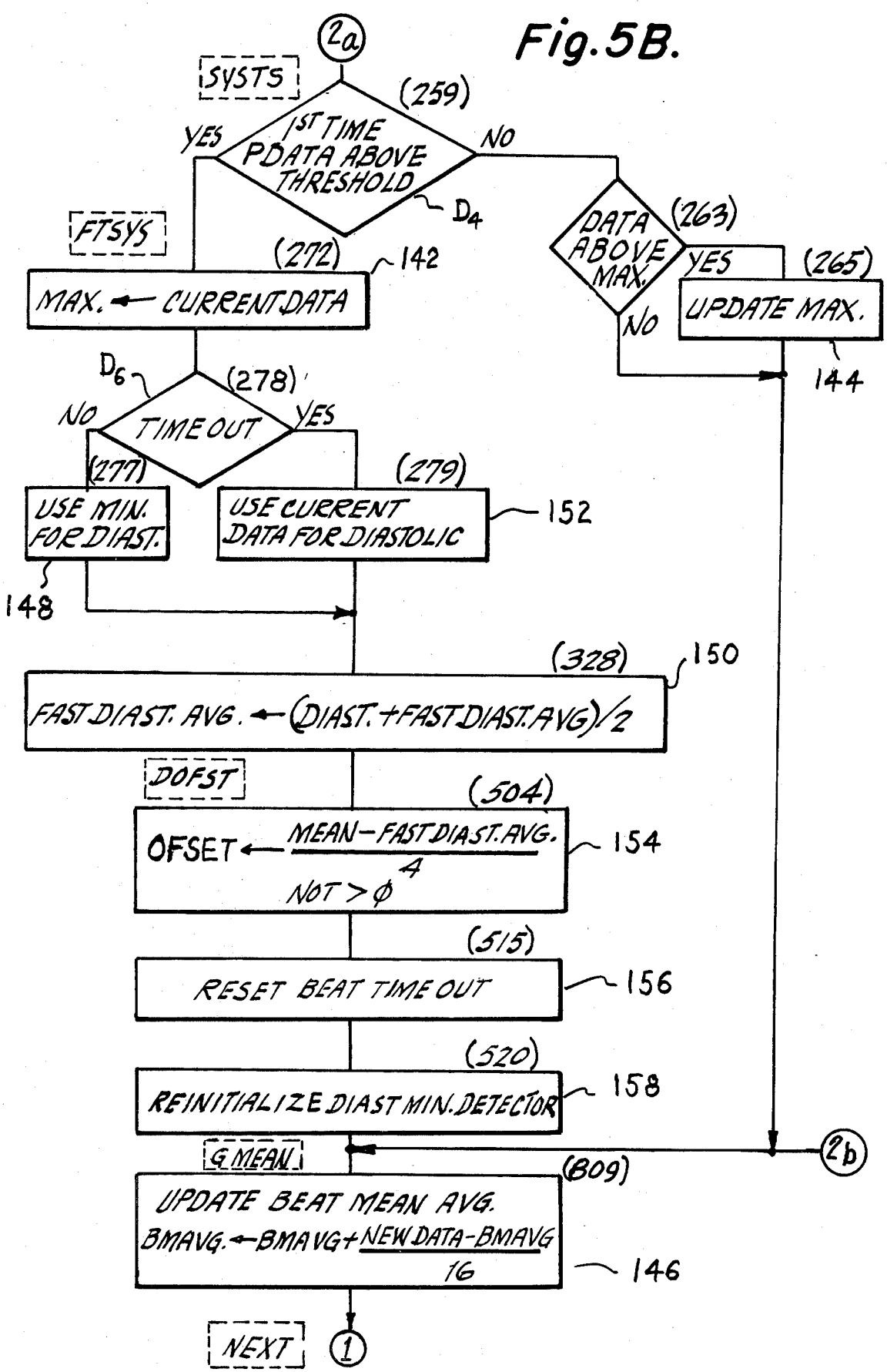
Figure 5C:
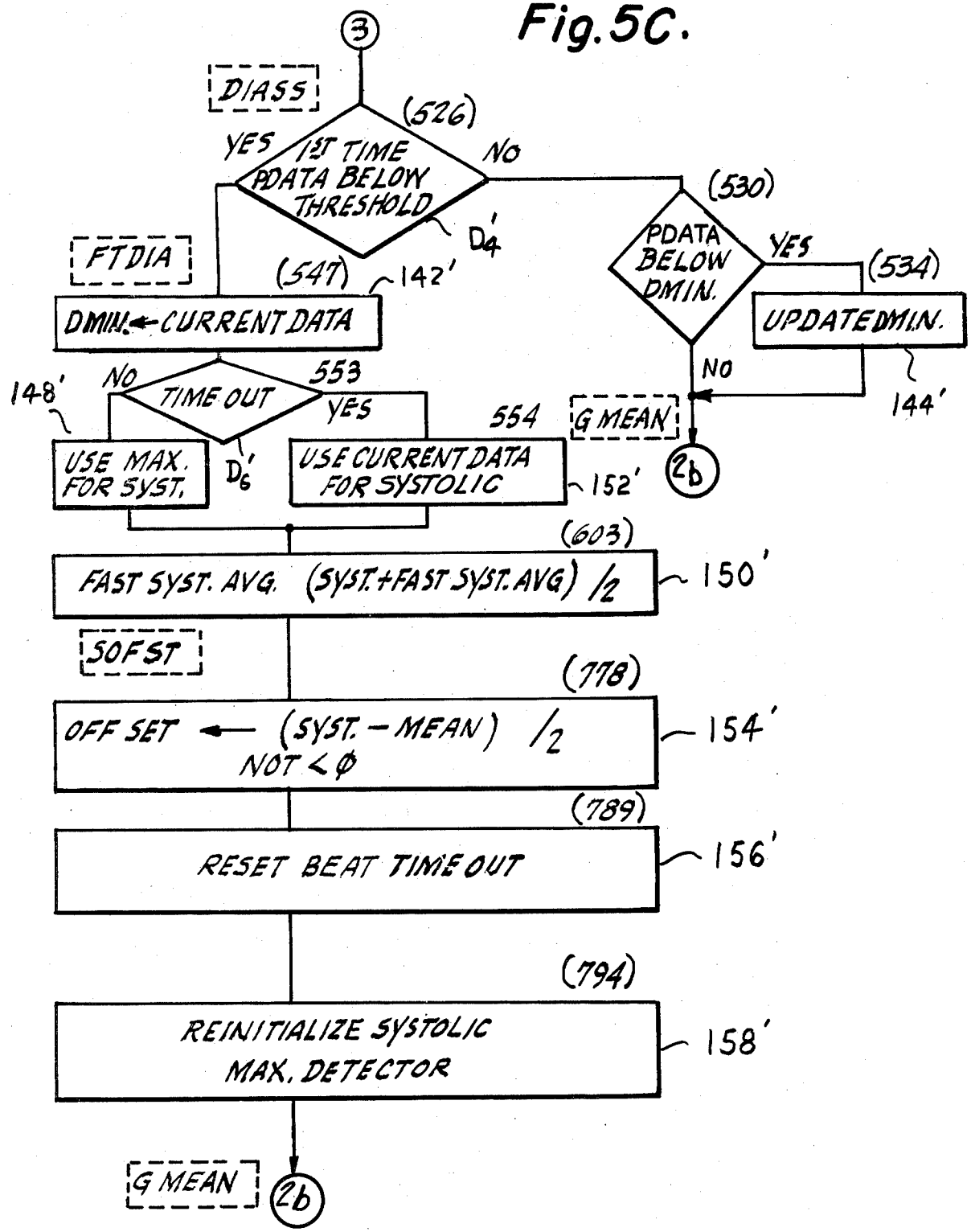

FIG. 3 includes graphs used in explaining the operation of the circuit of FIG. 2;

FIG. 4 is a block diagram of one form of computing means capable of carrying out the program set forth in the specification; and FIGS. 5A, 5B and 5C are flow charts for the program set forth in the specification.

Figure 1A:
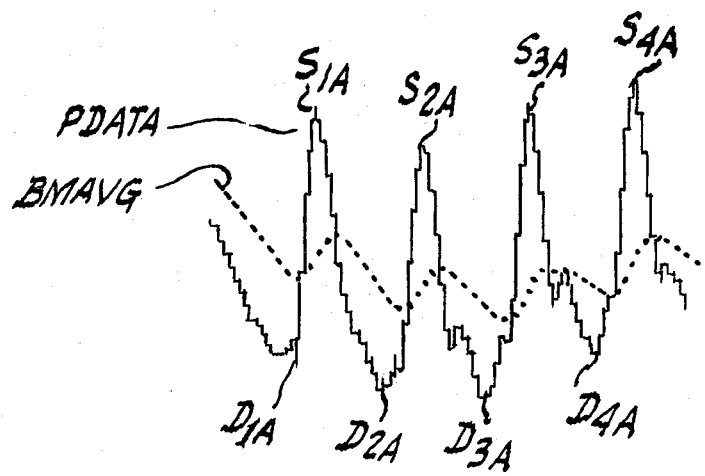
FIG. 1A is a graph of an actual blood pressure signal PDATA having perturbations of such small amplitude that they do not cross its mean BMAVG.
Figure 1B:
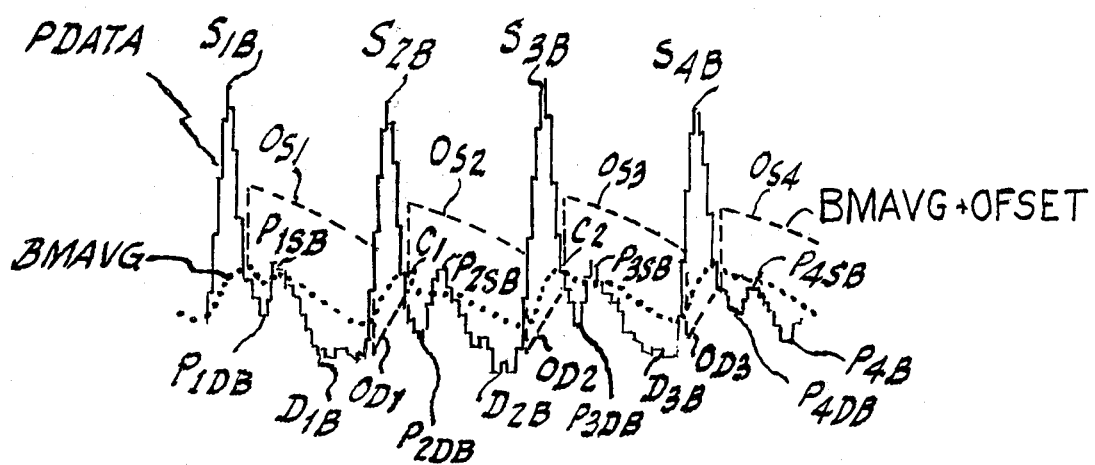
FIG. 1B is a graph of an actual blood pressure signal PDATA having perturbations of sufficient amplitude to cross its mean BMAVG. Also shown are offsets provided in accordance with this invention.

Before proceeding with a discussion of the various kinds of apparatus for processing the blood pressure signal so as to derive signals representative of the systolic and diastolic pressures in accordance with this invention, reference is made to the graphs of actual blood pressures shown in FIGS. 1A and 1B for an understanding of the overall functions to be performed. The solid lines designated by PDATA are the blood pressure signals and the dotted lines designated by BMAVG are their approximate means.

By inspection of FIG. 1A, it can be seen that the true systolic peaks are $S_{1A}$, $S_{2A}$, $S_{3A}$ and $S_{4A}$ and that the true diastolic peaks are $D_{1A}$, $D_{2A}$, $D_{3A}$ and $D_{4A}$. Perturbations or fluctuations in the blood pressure signal PDATA are of such small amplitude that the signal crosses its mean BMAVG only once between adjacent systolic and diastolic peaks. In accordance with one aspect of this invention, therefore, the values of the systolic peaks $S_{1A}$ through $S_{4A}$ can be determined by detecting the maximum value of the blood pressure signal PDATA during the time it is above the mean BMAVG and outputting each value as a separate systolic reading. The values of the diastolic peaks $D_{1A}$ through $D_{4A}$ can be determined by detecting the minimum value of the blood pressure wave PDATA during the time it is below the mean BMAVG and outputting each of the values as a separate diastolic reading.

In FIG. 1B, however, the positive perturbation peaks $P_{1SB}$, $P_{2SB}$ and $P_{3SB}$ extend above the mean BMAVG so that they would be detected as false systolic values and the negative peturbation peaks $P_{1DB}$, $P_{2DB}$ and $P_{3DB}$ would be detected as false diastolic values. In order to prevent this from occurring, offsets are alternately added to and subtracted from the mean BMAVG so as to form a dashed offset wave, BMAVG+OFSET, having alternate positive and negative offsets $O_{S1}$, $O_{D1}$, $O_{D2}$, $O_{S3}$, $O_{D3}$ and $O_{S4}$. Means for detecting a minimum peak is enabled whenever the blood pressure signal PDATA drops below the offset wave, and means for detecting a maximum peak is enabled when the blood pressure signal PDATA increases above the offset wave. The perturbation peaks $P_{1SB}$, $P_{2SB}$ and $P_{3SB}$ that were previously detected so as to yield false systolic pressure values because they exceeded the mean BMAVG are not detected because they do not exceed the offsets $O_{S1}$, $O_{S2}$ and $O_{S3}$. Perturbation peak $P_{4SB}$ does not exceed the mean BMAVG so that it would not cause a false systolic peak to be measured in either case. Negative perturbation peaks that occur while the maximum peak detecting means is activated are prevented from activating the minimum peak detecting means so as to produce false diastolic measurements by the negative offsets $O_{D1}$, $O_{D2}$ and $O_{D3}$.

Processing the blood pressure signal PDATA so as to provide the offsets referred to and to activate the peak detectors whenever the blood pressure signal crosses the offset wave BMAVG+OFSET can be effected by an analog circuit such as that shown in FIG. 2 or by the signal processing section of a computer. A program for this purpose that may be used with the Hewlett-Packard 21MX series computer is presented at the end of the specification, and the flow charts therefor are set forth in FIGS. 5A, 5B and 5C.

In the circuit of FIG. 2, variations in the blood pressure of a patient P such as represented by the wave PDATA in FIG. 3 are conveyed by a catheter 2 to a transducer $T_R$ that produces a corresponding electrical blood pressure signal PDATA. After amplification in an amplifier 4, the signal PDATA is applied to an input terminal 6 of the signal processing circuit. The terminal 6 is connected to a series combination of a resistor 8 and a capacitor 10 that form a low pass filter for providing at their junction 12 a voltage such as illustrated by the wave BMAVG of FIG. 3 that is the approximate mean of the blood pressure signal PDATA. A buffer amplifier 14 couples the signal BMAVG from the junction 12 to one input of an adder 16, and its other input is connected to a switch arm $s_1$. In the position shown, the switch arm $s_1$ is in contact with a terminal 18 to which a negative offset voltage, OFSET, may be applied in a manner to be described, and in its other position, it is in contact with a terminal 20 to which a positive offset voltage, OFSET, may be applied in a manner to be described. Thus, as illustrated in FIG. 3, an offset wave BMAVG+OFSET comprised of alternately positive and negative offsets to the mean BMAVG, such as $O_{SA}$, $O_{DA}$, $O_{SB}$ and $O_{DB}$, appears at the output of the adder 16. The output of the adder 16 is applied to the inverting input of an amplitude comparison means 22, and the PDATA signal from the input terminal 6 is applied to its non-inverting input. A relay coil 24 that operates switches $s_1$, $s_2$ and $s_3$ is connected between the output of the comparator 22 and a point of voltage $+V$.

When the PDATA signal crosses above the offset wave BMAVG+OFSET, the output of the comparator 22 becomes $+V$ volts, as indicated in the waveform 26, and the relay coil 24 is de-energized so as to permit the switches $s_1$, $s_2$ and $s_3$ to move to the upper positions shown where they are respectively in contact with the terminals 18, 28 and 30. When the PDATA signal crosses below the offset wave BMAVG+OFSET, the output of the comparator 22 is $-V$ volts, as indicated in the waveform 26, and the relay coil 24 is energized so as to move the switches $s_1$, $s_2$ and $s_3$ from the position illustrated into contact with the lower terminals 20, 32 and 34, respectively.

When the switches $s_1$, $s_2$ and $s_3$ are in the upper position shown, the switch $s_1$ is in contact with the terminal 18 so as to apply a negative OFSET voltage to the adder 16; the switch $s_2$ is in contact with the terminal 28 so as to apply a voltage $+V$ to an input of an AND gate 36; and the switch $s_3$ is in contact with the terminal 30 so as to apply the PDATA signal to a maximum peak detector 38. When the switches $s_1$, $s_2$ and $s_3$ are in their lower positions, the switch $s_1$ is in contact with the terminal 20 so as to apply a positive OFSET voltage to the adder 16; the switch $s_2$ is in contact with the terminal 32 so as to apply the $+V$ voltage to an input of an AND gate 40; and the switch $s_3$ is in contact with the terminal 34 so as to apply the PDATA signal to a minimum peak detector 42.

The output of the maximum peak detector 38 is connected to a sample-and-hold circuit 44, and its output is connected to a strip chart recorder 46 or other display means. The output of the maximum peak detector 38 is also connected to the following circuits for deriving a negative OFSET voltage to be applied to the terminal 18 associated with the switch arm $s_1$. The inverting input of a comparator 48 is connected to the output of the maximum peak detector 38, and the non-inverting input is connected to a point of $-V$ volts. In a manner to be explained, the output of the maximum peak detector 38 is made to have a voltage of $-V$ volts for some time before the switches $s_1$, $s_2$ and $s_3$ move to their upper positions so that during this time both inputs of the comparator 48 are at $-V$ volts. Its output is therefore positive, and it is positive long enough for the voltage $+V$ to have passed through a delay means 50 to one input of the AND gate 36. When the switches $s_1$, $s_2$ and $s_3$ move to their upper positions, the switch $s_2$ contacts the terminal 28 so as to apply a voltage $+V$ to the other input of the AND gate 36 and cause its output to become positive. The voltage $-V$ is selected to be more negative than the output of the maximum peak detector 38 will ever be in response to a blood pressure signal PDATA, so that when the switch $s_3$ contacts the terminal 30 so as to apply the PDATA signal to the maximum peak detector 38, its output becomes positive with respect to $-V$. As a result, the voltage at the output of the comparator 48 becomes negative, and after a time determined by the delay means 50, it reaches the AND gate 36, causing its output to drop. Thus, the output of the AND gate 36 is a positive control pulse having a duration of the delay of the delay means 50.

This positive control pulse is applied to a sample-and-hold means 52 so as to cause it to output a steady voltage equal to the voltage at the output of the minimum peak detector 42 to which it is coupled. The control pulse is also applied via a delay means 54 and a diode $d_1$ to means such as shown in FIG. 2A, that is included within the minimum peak detector 42, for setting its output voltage at a voltage $+V$ that is more positive that it will ever become in response to the signal PDATA. In the simplified diagram of FIG. 2A, the peak detector 42 is illustrated as being comprised of a diode $d_{42}$ having the blood pressure signal PDATA applied to its cathode and its anode connected to ground by a capacitor $C_M$. The gate of an FET transistor 56 is connected to the diode $d_1$. When the delayed positive control pulse is applied to the gate electrode, the capacitor $C_M$ is charged to the positive voltage $+V$. The purpose of the delay 54 is to permit the sample-and-hold means 52 to output the minimum voltage of the peak detector 42 before its output is charged to $+V$.

In order to derive the negative OFSET voltage, the positive control pulse provided by the AND gate 36 is applied to a relay coil 58 so as to close a normally open switch $s_4$ and connect the output of the sample-and-hold circuit 52 to an integrator comprised of a resistor 60 and a capacitor 62 connected in series. Depending on the duration of the pulse and the RC time constant of the resistor 60 and the capacitor 62, the voltage FDAVG across the capacitor 62 can be made to be a desired exponentially weighted average emphasizing the most recent diastolic values outputted by the sample-and-hold circuit 52. It has been found satisfactory to charge the capacitor 62 by half the voltage that is across the resistor 60 at the beginning of a control pulse. The voltage FDAVG is applied to the Y input of a subtractor 64, and the wave BMAVG at the output of the amplifier 14 is applied to the X input. The output of the subtractor 64, Y-X, is therefore the difference between the voltage FDAVG and the approximate mean BMAVG of the blood pressure signal PDATA. The difference is always negative. In order to hold onto this difference in voltages, the output Y-X of the subtractor 64 is coupled to a sample-and-hold circuit 66 that is also triggered by the control pulse from the AND gate 36. A given fraction of the voltage at the output of the sample-and-hold circuit 66 is selected by coupling a potentiometer resistor 68 across the output of the sample-and-hold circuit 66 and setting its tap 70. The negative voltage at the tap 70 is the OFSET voltage that is applied to the terminal 18. A fixed negative OFSET can be provided by connecting a switch $s_6$ to the tap of a potentiometer 71 that is connected between a point of negative potential and ground.

The output of the maximum peak detector 42 is connected to the sample-and-hold circuit 52, and its output is applied to the recorder 46. The output of the minimum peak detector 42 is also connected to the following circuits for deriving a positive OFSET voltage to be applied to the terminal 20 associated with the switch $s_1$. The non-inverting input of a comparator 72 is connected to the output of the maximum peak detector 42 and its inverting input is connected to a point of +V volts. It will be remembered that the output of the detector 42 was set at a voltage +V in response to the control pulse from the AND gate 36 when the switches $s_1$, $s_2$ and $s_3$ moved to their upper positions, and that +V is more positive than the output of the minimum peak detector 42 will ever be. Thus, both inputs of the comparator 72 are positive and its output also is positive. It is positive long enough for its positive output voltage to have passed through a delay means 74 and to have reached an input of the AND gate 40. Thus, when the switch $s_2$ moves to its lower position so as to apply the voltage +V to the terminal 32, both inputs of the AND gate 40 are positive and its output is therefore positive. At the same time, the switch $s_3$ is moved into contact with the terminal 34 so as to apply the signal PDATA to the input of the minimum peak detector 42. Its output immediately becomes less than the voltage +V so that the output of the comparator 72 now becomes negative. When this negative voltage passes through the delay means 74 to the AND gate 40, its output drops. Therefore, the AND gate 40 outputs a positive control pulse just after the switches $s_1$, $s_2$ and $s_3$ move to their lower positions. The duration of the pulse equals the delay of the delay means 74.

This positive control pulse is applied to the sample-and-hold means 44 so as to cause it to output a steady voltage equal to the voltage at the output of the maximum peak detector 38 to which it is coupled. The pulse is also applied via a delay means 76 and a diode $d_2$ to means such as shown in FIG. 2B for setting the output voltage of the maximum peak detector 38 at a voltage −V that is more negative than it will ever become in response to the signal PDATA. In the simplified diagram of FIG. 2B, the peak detector 38 is illustrated as being comprised of a diode $d_{38}$ having the blood pressure signal PDATA applied to its anode and its cathode connected to ground via a capacitor C'M. The gate of an FET transistor 78 is connected to the diode $d_2$. When the delayed positive control pulse is applied to the gate electrode, the capacitor $C_M'$ is charged to the negative voltage −V.

In order to derive the positive OFSET voltage, the positive control pulse provided by the AND gate 40 is applied to a relay coil 82 so as to close a normally open switch $s_5$ and connect the output of the sample-and-hold circuit 44 to an integrator comprised of a resistor 84 and a capacitor 86 connected in series. Depending on the duration of the pulse and the RC time constant of the resistor 84 and the capacitor 86, the voltage FSAVG across the capacitor 86 can be made to be a weighted average emphasizing the most recent systolic values outputted by the sample-and-hold circuit 44. It has been found satisfactory, however, to charge the capacitor 86 by half the voltage that is across the resistor 84 at the beginning. The voltage FSAVG is applied to the Z input of a subtractor 88, and the wave BMAVG at the output of the amplifier 14 is applied to the X' input. The output of the subtractor 88, Z-X', is therefore the difference between the voltage FSAVG and the approximate mean BMAVG of the blood pressure signal PDATA during the pulse. The difference is always positive. In order to hold onto the difference, the output of Z-X' of the subtractor 88 is coupled to a sample-and-hold circuit 90 that is also triggered by the pulse from the AND gate 40. A given fraction of the voltage, Z-X', at the output of the sample-and-hold means 90 is selected by coupling a potentiometer resistor 92 across the output of the sample-and-hold circuit 90 and setting its tap 94. The positive voltage at the tap 94 is the OFSET voltage that is applied to the terminal 20. A fixed positive OFSET voltage can be provided by connecting a switch $s_7$ to the tap of a potentiometer 95 that is connected between a point of positive potential and ground.

INITIALIZATION

After electrical power is applied to the circuit by any suitable means, a switch $s_8$ is closed so as to apply a positive voltage from a battery 96 to an input of the inclusive OR gate 98, causing it to output a positive pulse of voltage via diode $d_3$ to the means, such as shown in FIG. 2B in the maximum peak detector 38, for setting the output of the detector at −V volts. The positive pulse of voltage is also applied via a diode $d_4$ to means, such as shown in FIG. 2A in the minimum peak detector 42, for setting its output at a voltage +V. The pulse at the output of the OR gate 98 is also applied to a relay coil 100 so as to close normally open switches $s_9$, $s_{10}$ and $s_{11}$ for the duration of the pulse. One side of each of the switches is connected to receive the blood pressure signal PDATA from the input terminal 6, and the other sides are respectively connected to the ungrounded plates of the capacitors 10, 62 and 86. Thus, if, as indicated in FIG. 3, the switch $s_8$ is closed at the time $t_0$, the capacitors will all be charged to a voltage of the point $P_0$ in the blood pressure signal PDATA.

LOSS OF DATA

If, for one reason or another, the blood pressure signal PDATA fails, the circuit is automatically re-initialized by the following circuits. The outputs of the AND gates 36 and 40 are respectively connected to the inputs of an OR gate 102. Whenever a pulse is supplied by one of the AND gates, the OR gate 102 outputs a positive pulse to a reset terminal of a timer 104. If the pulses from the OR gate 102 are spaced by less time than the setting of the timer 104, it is repeatedly reset before it can reach its limit, but if the space between two consecutive pulses from the OR gate 102 exceeds the setting of the timer 104, it will reach its limit and output a positive pulse. This is applied to a different input of the OR gate 98 to which the switch $s_8$ is connected so as to cause the OR gate 98 to output a positive pulse and energize the relay coil 100.

PULSE RATE COUNTER

The pulse rate of the patient P can be indicated by connecting a counter 106 to the output of the comparator 22.

OVERALL OPERATION

Assume that the initialization switch $s_8$ is closed at the time $t_0$ shown in FIG. 3. As previously stated, the capacitors 10, 62 and 86 will be charged to a voltage $P_0$. Inasmuch as the signal PDATA becomes more positive after the time $t_0$, the voltage across the capacitor 10 gradually increases along a transient curve T until it merges with the approximate mean BMAVG of the signal PDATA. Immediately after the time $t_0$, the output of the comparator 22 is positive so that the switches $s_1$, $s_2$ and $s_3$ remain in their upper positions. The switch $s_2$ is in contact with the terminal 28 so as to apply the voltage $+V$ to one input of the AND gate 36, but because no positive voltage is applied to the other input, its output remains at a low voltage. The switch $s_1$ is in contact with the terminal 18, but no voltage is applied to it because the X and Y inputs to the subtractor 64 are both equal to $P_0$ at the time $t_0$.

When, however, the signal PDATA drops below the transient T at the time $t_1$, the output of the comparator 22 becomes negative, energizing the relay coil 24 and causing the switches $s_1$, $s_2$ and $s_3$ to move to their lower positions. The AND gate 40 outputs a control pulse $A_1$ in the manner previously explained. This triggers the sample-and-hold circuit 44, causing it to output a voltage equal to the voltage of the systolic peak $S_1$, as indicated by the line $VS_1$. It also energizes the relay coil 82 so as to cause the voltage across the capacitor 86 to have a vlaue $FSAVG_1$ that is halfway between the value $VS_1$ and $P_0$. The subtractor 88 produces a positive output voltage that is equal to the difference between $FSAVG_1$ and the voltage across the capacitor 10 at the time $t_1$, the latter being the voltage of the merging waves T and BMAVG. The sample-and-hole circuit 90 is triggered by the pulse $A_1$ so as to output this voltage until is triggered again. Some fraction of this voltage, such as one-half, is selected by the tap 70 and applied via the terminal 20 and the switch $s_1$ to the adder 16 wherein it is added to the wave BMAVG to produce the offset section $O_{SA}$. Because the perturbation peaks $PAS_1$ and $PAS_2$ do not extend above the offset $O_{SA}$, they are not detected and cause no problem.

When, however, the signal PDATA crosses above the offset $O_{SA}$ at the time $t_2$, the switches $s_1$, $s_2$ and $s_3$ move back to the upper position shown and cause the AND gate 36 to output a pulse $A_2$. This pulse triggers the sample-and-hold circuit 52 and causes it to output a voltage equal to the output of the minimum peak detector 42, which is equal to the voltage $VD_1$ of the diastolic peak $D_1$. At the same time, the control pulse $A_2$ energizes the relay coil 58 and causes a voltage $FDAVG_2$, which is halfway between the voltage of the diastolic peak $D_1$ and the voltage $P_0$, to appear across the capacitor 62. The subtractor 64 derives a negative voltage equal to the difference between the voltage $FDAVG_2$ and the voltage of the wave BMAVG at the time $t_2$. This voltage is retained by the sample-and-hold circuit 66, and a fraction of it, such as one-quarter, is selected by the tap 70 and applied via the terminal 18 and the switch $s_1$ to the adder 16. Because it is negative so as to be subtracted from the wave BMAVG, the resulting OFSET voltage is such that the offset section $O_{DA}$ is below the wave BMAVG. Note that the perturbation peak $PAD_3$ that extends below the wave BMAVG does not extend below the offset $O_{DA}$ so that it is not detected as a false diastolic value.

When the signal PDATA drops below the offset $O_{DA}$ at time $t_3$, the AND gate 40 outputs a pulse $A_3$ to the sample-and-hold circuit 44, and it outputs the voltage $VS_2$ of the systolic peak $S_2$. The voltage across the capacitor 86 is $FSAVG_3$, which is halfway between $VS_2$ and $FSAVG_1$. The subtractor 88 outputs a voltage equal to the difference between the voltage of $FSAVG_3$ and the voltage of BMAVG at the time $t_3$. One-half of the difference is selected by the tap 94 and applied via terminal 20 and the switch $s_1$ to the adder 16 so as to form an OFSET voltage such that the offset section $O_{SB}$ is above the wave BMAVG. Once again, perturbation peaks, such as $PAS_4$ and $PAS_5$, do not extend above the offset $O_{SB}$ so that they are not detected.

Finally, when the PDATA signal crosses above the offset $O_{SB}$ at the time $t_4$, the switches $s_1$, $s_2$ and $s_3$ return to their upper positions. The AND gate 36 outputs a control pulse $A_4$ to the sample-and-hold circuit 52, and it outputs a voltage of $VD_2$ equal to the voltage of the diastolic peak $D_2$. The voltage across the capacitor 62 is $FDAVG_4$, which is halfway between the voltage of the diastolic peak $D_2$ and the voltage of $FDAVG_2$. The subtractor 64 outputs a voltage equal to the difference between the voltage of $FDAVG_4$ and the voltage of BMAVG at the time $t_4$. One-quarter of this difference is selected by the tap 70 and applied via the terminal 18 and the switch $s_1$ to the adder 16 so as to form an OFSET voltage such that the offset section $O_{DB}$ is below the wave BMAVG.

COMMENT

Whereas the value of the OFSET applied to the adder 16 has been derived by momentarily closing the switches $s_4$ and $s_5$, similar results can be attained if they are permanently closed by selecting suitable time constants for the low pass filters 60, 62 and 84, 86.

It would also be possible to use other criteria for relating the values of the OFSET voltages to be added to or subtracted from BMAVG in the adder 16 to prior portions of the signal, e.g., the positive value of OFSET could be a selected portion of the average amplitude of a number of maximum peaks, and the negative value of OFSET could be a selected portion of the average amplitude of a number of minimum peaks. It is possible to use only one value of OFSET, the other value being set to zero. And, as pointed out, fixed values of OFSET can be provided by the potentiometers 71 and 95. Whatever criteria is used, the greater the OFSET, the less is the likelihood of producing erroneous systolic and diastolic values by detecting peaks due to perturbations, but as the OFSET becomes larger, the possibility of missing a maximum or minimum representing a true systolic or diastolic peak increases.

In the embodiments of the invention herein disclosed, PDATA is applied to the switch s₃, but it will be understood that this signal could undergo various preprocessing before being applied to apparatus for selecting the maximum and minimum values in accordance with the invention.

As illustrated, the maximum and minimum peaks are those that respectively have the greatest departure from BMAVG, but they could be selected on the basis of other criteria and applied to the capacitors $C_M'$ and $C_M$ of FIGS. 2B and 2A, respectively. For example, a width criteria might be used in addition to a height criteria in selecting maximum or minimum peaks, or a boxcar filter might be inserted at the inputs of the peak detectors 38 and 42. Whatever type of processing is used to determine the values of the systolic and diastolic pressure, this invention provides a means for identifying the intervals during which the search for each pressure should be performed. The positive and negative portions of the wave 26 at the output of the comparator 22 could be used for this purpose.

DESCRIPTION OF A DIGITAL SIGNAL PROCESSOR

Direct processing of the blood pressure signal PDATA at the output of the amplifier 4 of FIG. 2 so as to derive positive and negative peaks in accordance with this invention can be carried out by digital logic circuits as well as by the analog circuits of FIG. 2. Circuits operating in this manner are described in connection with the Hewlett-Packard 21MX series computer, but it will be apparent to those skilled in the art that other computers or other combinations of devices could be used. It is contemplated that the computer will be an integral part of the monitoring equipment of which this invention forms a part.

FIG. 4 is a block diagram of the functional digital units required for carrying out the invention. Control of the flow of data as well as the operations performed on the data is determined by instructions stored at different locations in a read only memory or a read/write memory 108. Instructions are fetched from the memory 108 by a memory controller 110 in response to addresses in a program counter or P register 112 and applied to a controller/sequencer 114 that causes the instructions to be carried out by other components of the computer. When each instruction has been carried out, the controller/sequencer 114 requests the next instruction from the memory controller 110, which retrieves the instruction according to the address in the P register. The analog blood pressure signal PDATA at the output of the amplifier 4 of FIG. 2 is converted into its digital form by an analog-to-digital converter 116 that samples the analog wave PDATA at intervals determined by a clocking device 118 which is distinct from a clock, not shown, contained in the controller/sequencer 114. The controller/sequencer 114 controls the transmission of the digitized PDATA via an input/output processor 119 to an A register accumulator 120 or a B register accumulator 122 that are part of an arithmetic processor including an arithmetic logic processor 124. The controller/sequencer 114 may also cause a memory controller 126 to take data from one of the accumulators 120 or 122 or the logic processor 124 and place it into a read/write data storage memory 128 or vice-versa. The data storage memory 128 may share the same physical memory with the control instruction memory 108, and both memories may be controlled by the same memory controller, but separate memories and controllers are shown so as to separately identify the roles played by each.

All operations involving data manipulation usually take place in the accumulators 120 or 122. A program instruction may, for example, cause the controller/sequencer 114 to request the arithmetic logic processor 124 to perform some operation involving one or both of the accumulators. Whether the operation includes adding, dividing, negating, multiplying, shifting, or rotating, Boolean manipulation (AND, OR), or testing, the results stay in an accumulator. If the value in the accumulator is to be stored in the data memory 128, a separate instruction will be given to the memory controller 126 by the controller/sequencer 114.

Instructions may be taken from the controller instruction memory 108 by the memory controller 110 with a desired sequence of steps by setting a different address in the program counter 112 with the arithmetic logic processor 124 or with the controller/sequencer 114, e.g., a test compare instruction could result in the contents of the program counter or P register 112 being modified so as to cause it to select an alternate branch in the stream of program instructions derived from the control instruction memory 108.

The external clock 118 provides asynchronous timing pulses to the input/output processor 119 causing it to inform the controller/sequencer 114. This results in the program counter 112 being shifted to a timing section of the program that might, for example, request the input/output processor 119 to sample the analog blood pressure signal PDATA with the A-D converter 116 and place it in the data memory 128 via one of the accumulators 120 or 122. After the timing section of the program is completed, the program counter 112 would be restored to its previous setting so as to allow the computer to resume its previous processing.

When all manipulations of data have been completed so as to derive a digital signal representative of a maximum or minimum peak of the blood pressure signal PDATA, the controller/sequencer 114 could issue a command signal causing the input/output processor 119 to apply the digital signal to a digital-to-analog converter 132 that converts it to an analog signal corresponding as required to a maximum peak at the output of the sample-and-hold circuit 44 of FIG. 2 or to a minimum peak at the output of the sample-and-hold circuit 52.

OPERATION OF THE DIGITAL PROCESSOR IN ACCORDANCE WITH THE INVENTION

The manner in which a Hewlett-Packard 21MX series computer processes a blood pressure signal PDATA so as to derive maximum peak values and minimum peak values in such manner as to significantly reduce the effects of perturbations will now be explained by reference to the flow charts of FIGS. 5A, 5B and 5C. Key steps in the program at the end of the specification that are related to blocks in the flow charts are set forth in nearby parentheses. Dashed boxes contain labels which are referenced in the computer program. Steps in the program that are indicated by an asterisk (*) are not actual computer steps, but are included for purposes of explanation. Reference will be made, where appropriate, to circuit components in FIG. 2 that perform functions carried out by the computer shown in FIG. 4, but identification of the figures referred to is not thought to be required in each case. Statements to the effect that certain functions are done by or in a block means that they are done by the relevant portion of the program and not actually by the blocks per se.

The digital form of the blood pressure signal PDATA at the output of the analog-to-digital converter 116 of FIG. 4 is transferred into the accumulator 120 by the block 134 of FIG. 5A. As only twelve significant bits are handled by the converter 116, the least significant four bits are set to zero because their values are not known. Negative blood pressures are not encountered so that if PDATA is negative, it must be due to an artifact. Therefore, if PDATA is negative, its value is arbitrarily set to zero.

If the equipment has just been turned on, as is done in the circuit by closing the switch $s_8$, this fact is indicated by a learning block $D_1$. In this event, the learning flag is cleared in block 136, which corresponds to opening the switch $s_8$. The equipment is then initialized by carrying out the functions indicated in block 138. In this block, a timer, which has some arbitrary limit such as five seconds, is set to zero. This function is performed in the circuit by applying a pulse from the OR gate 102 to the timer 104. The output of the maximum peak detector in the computer is set at some unique value that represents a pressure far less than the maximum peak detector will ever experience, and the minimum peak detector is set at some unique value representing a pressure far greater than it will ever experience. This corresponds to the application of pulses to the detectors 38 and 42 of FIG. 2 via the diodes $d_3$ and $d_4$. Finally, the values of FSAVG and FDAVG, as well as BMAVG, are set at the value $P_0$ of PDATA at the time $t_0$. In the circuit, this is done by closure of the switches $s_9$, $s_{10}$ and $s_{11}$.

Then, as indicated in the block 140, an offset, OFSET, is added to BMAVG, but if the initialization procedures above have just been carried out, the value of OFSET is zero because FSAVG, FDAVG and BMAVG have all been set to the initial value $P_0$ of PDATA in the block 138.

If, however, decision block $D_1$ indicates that the apparatus is not to be initialized, a test is made in a decision block $D_2$ as to whether the arbitrarily selected time limit has elapsed since the last new output of SMAX or DMIN has occurred. If so, the initialization procedures of block 138 are repeated.

On the other hand, if the decision block $D_1$ indicates that the apparatus is not to be initialized and the test in block $D_2$ indicates that the arbitrarily selected time limit has not elapsed since the last new output of SMAX or DMIN, the value of OFSET to be calculated in a manner to be explained is other than zero and is added to BMAVG.

At this point, a test is made for each sample of PDATA in a decision block $D_3$ as to whether it is above or below the threshold BMAVG+OFSET. If the equipment has just been initialized, the value of OFSET is zero for reasons set forth above. If PDATA is above the threshold, the operation proceeds as indicated after point (2a) in the flow chart and, therefore, in accordance with FIG. 5B; and if PDATA is below the threshold, the operation proceeds as indicated at point (3) in the flow chart and, therefore, in accordance with FIG. 5C.

SYSTOLIC DETECTION AND NEGATIVE OFFSET

As indicated in decision block $D_4$, a test is to be made as to whether each sample of PDATA is the first that is above the reference BMAVG+OFSET. If the equipment has just been initialized, the output, SMAX, of the maximum peak detector, which is stored in the data memory 128 of FIG. 4, will be at the arbitrarily selected unique value previously referred to. With this unique value of SMAX, the test will indicate that the first sample indicated by $D_3$ as being higher than the reference is the first that is above the threshold. When this occurs, processing block 142 causes SMAX to be changed from the unique value to the value of this new sample of PDATA. Therefore, when the next sample of PDATA is tested in $D_4$, SMAX no longer has the unique value referred to, so that the test will indicate that this is not the first sample above threshold. If the equipment has not just been initialized, the output, SMAX, of the maximum peak detecting means is set at the unique value by the block 158' of FIG. 5C. This occurs when PDATA first drops below the reference level. Then, when it again crosses above the reference, the first sample of PDATA above the threshold is identified as has just been described.

When $D_4$ indicates that the first sample of PDATA above the threshold has been received, the operations on the left side of FIG. 5B are carried out, but before describing them, attention is given to the manner in which the computer operates as a maximum peak detector like 38 of FIG 2. When the second sample of PDATA that is above the threshold arrives, the test in $D_4$ will indicate that it is not the first sample above threshold because block 142 has replaced the unique value of SMAX in the data memory 128 with a value representing the amplitude of the first sample. When this occurs, a test is made in a decision block $D_5$ to determine whether the second sample is greater than the first. If it is, a block 144 updates SMAX and one proceeds to point (2b) in the flow chart that is labeled GMEAN in the program. If the new sample is not above SMAX, one also proceeds to the same point. At point (2b), as indicated by the block 146, a new value of BMAVG is calculated.

Return now to the operations that result from the determination by $D_4$ that a sample is the first above the reference. A decision block $D_6$ tests whether or not a time-out has occurred, a function performed by the OR device 98 in the circuit of FIG. 2. If not, the value of DMIN that was previously determined in accordance with FIG. 5C is used, as indicated by a block 148, as the diastolic value in the calculation of the fast diastolic average, FDAVG, performed in the block 150. In the circuit, FDAVG is developed across the capacitor 62. If a time-out has occured, the current value of PDATA is used for this purpose, as indicated by a block 152.

In block 154, the value of OFSET that is to be subtracted from BMAVG is calculated. In the circuit, this is done by the subtractor 64 and the potentiometer 68 and applied to the adder 16 via the switch $s_1$.

In block 156, the timer is reset. In the circuit, this is done by the OR gate 102.

The minimum peak detector of the computer is reset as indicated in the block 158 to a unique value that is greater than the detector will ever experience. In the circuit, this function is performed by application of a control pulse from the AND gate 36 to the minimum peak detector 42 via the delay 54 and the diode $d_1$.

If the minimum value of DMIN occurring between downward and upward crossings of the threshold BMAVG+OFSET by PDATA is required, it will be the value of DMIN stored in the data memory 128 at the time when $D_4$ indicates that the first sample above threshold has been received. It can therefore be obtained between the steps performed by the block 148 and the re-initializing of the minimum peak detector in the block 158. There is no direct equivalent of the sample-and-hold circuits 44 and 52 in the circuit of FIG. 2 because the values of DMIN can be stored in a memory.

DIASTOLIC DETECTION AND POSITIVE OFFSET

If the test in the decision block $D_3$ of FIG. 5A indicates that the blood pressure signal PDATA is less than the threshold BMAVG+OFSET, the next step in the procedure is at $D_4'$ at the top of FIG. 5C. The blocks in FIG. 5C are designated by the same numbers primed as in FIG. 5B because they correspond in function but operate with different signals, as indicated. A key step in the program that is pertinent to each block is indicated in nearby parentheses. The decision block $D_4'$ corresponds in function to the decision block $D_4$ of FIG. 5B, but instead of determining whether it is the first time PDATA is above the threshold, it determines whether it is the first time PDATA is below the threshold. The decision block $D_5'$ and the block 144' operate as a minimum peak detector and the minimum value to which they compare samples of PDATA is stored in the data memory 128 by the block 142'. If a time-out is detected by a decision block $D_6'$, the block 152' provides the current value of PDATA for the systolic value in the calculation of FSAVG in the block 150'. If there has not been a time-out, the block 148' provides the value of the systolic value SMAX to be used in the calculation of FSAVG in the block 150'. The positive OFSET is claculated by the block 154', and the timer is reset by the block 156'. Re-initialization of the means for detecting a maximum peak so that its output is the unique value referred to in the discussion of FIG. 5B, a value that is less than the detector will ever experience, is performed by the block 158'. A new value of BMAVG is then calculated in the block 146 of FIG. 5B. It is analogous to the integration performed by the capacitor 10 during the negative peaks of PDATA.

The maximum value of SMAX occurring between consecutive upward and downward corssings of the threshold BMAVG+OFSET by PDATA represents the systolic blood pressure. It is the value of SMAX stored in the data memory 128 at the time when $D_4'$ of FIG. 5C indicates that the first sample below threshold has been received. It can therefore be obtained between the steps performed by the block 148' and the re-initialization of the maximum detector in the block 158'.

EXAMPLE CALCULATION

That the hardware of the computer is controlled in a manner that is fully equivalent to the operation of the hardware represented in the schematic diagram of FIG. 2 will now be illustrated by an example. Reference will be made to the block diagram of the computer illustrated in FIG. 4 when appropriate.

Let us consider the resistor 8 and capacitor 10 that filter the input value PDATA to derive its approximate mean BMAVG. The equivalent function is performed by the computer program steps 809 through 819 that occur at the label GMEAN in the program and on the flow chart. The mathematical basis of this computation is described in lines 800 to 807 of the program. It may be shown that, if this computation is performed at a regular interval with a value of PDATA representing the input to the RC filter 8, 10, the value BMAVG derived by the computer will behave identically as a function of time to the voltage BMAVG on the capacitor 10.

This computation is implemented in the computer as follows. The instruction on line 809 causes the memory controller 126 to retrieve the numeric value representing BMAVG from the data storage memory 128 and enter this value into the A register 120. The next instruction on line 810 causes the contents of the A register 120 to be negated. The instruction on line 811 causes the value PDATA to be retrieved from the data memory 128 and added to the contents of the A register 120, the result, PDATA−BMAVG, remaining in that register. The instructions on lines 812 and 813 cause the contents of the A register to be shifted to the right four places. This results in the binary value, PDATA−BMAVG, being divided by 16. This operation is performed by the arithmetic and logic processor 124 of the computer and the results remain in the A register. The next two instructions are provided to prevent deadband when the divisor has a value lying between 0 and 15, and is therefore not represented in the RC equivalent. In line 818, the instruction causes the value BAMVG to be fetched from memory 128 by the memory controller 126 and added to the A register accumulator. The instruction on line 819 causes the contents of the A register to be stored back into memory 128, replacing and updating the original value of BMAVG.

This process takes place for each new sample of PDATA which is acquired by the analog-to-digital converter at an arbitrary rate. A rate of 50 samples per second has been found to be suitable.

If we examine the RC filter formed by resistor 84 and capacitor 86 of FIG. 2, we see that its function may be duplicated in a similar manner. In this case, the filter value represented by the voltage on the capacitor 86 is updated once each heartbeat, rather than as a function of time. This is also done in FIG. 2. We may note that the filter formed by resistor 8 and capacitor 10 is always connected to the input, and that it integrates or smooths the data as a function of time, whereas the RC filter formed by resistor 84 and capacitor 86 is only intermittently connected to its input signal by switch $s_5$, which is activated once each beat for a uniform time interval by relay coil 82. By this means, the RC filter 84, 86 is shown to be updated once per beat instead of uniformly as a function of time. This filter is implemented in the computer program by the instructions on lines 603 through 606. The function relating to the RC filter 60, 62 are carried out in a similar manner.

Program to be Used with
a Hewlett-Packard 21MX Series Computer

```
0157   *
0158   *    GET NEXT DATA POINT FROM PRESSURE BUFFER
0159   *
0160   *
0161   NEXT  LDX PPHCO
0162   *
0173         LDA 0,I      GET DATA
0174   *
0179   *
0180   *
0181         AND =B177760  STRIP 4 LSB'S
0182         SSA
0183         CLA           DON'T ALLOW NEGATIVE
0184         STA PDATA
0185   *
0186   *
0187   *      CHECK FOR LEARNING BIT SET
0188   *         IF SET USE CURRENT DATA FOR STATUS DISPLAY
0189   *         STARTING VALUES.
0190   *
0191   *
0192         LDA LEARN
0193         CLF 3
0194         AND PCTPT,I   PC0
0195         SZA,RSS
0196         JMP NOLRN
0197   *
0198         CMA
0199         AND PCTPT,I   CLEAR LEARNING BIT
0200         STA PCTPT,I
0201         STF 3
0207   *
0208         JMP TOUT
0209   *
0210   NOLRN STF 3
0211   *
0212   *
0213   *
0214   *       CHECK FOR TIME OUT ON BEAT DETECTION
0215   *
0216         LDB OFSET
0217         ISZ BCNTR
0218         JMP S/D?
0219   *
0220   *                   TIMEOUT!
0221   *    NO BEATS FOUND -  RESET ALL ANALYSIS
0222   *
0223   *    1 SECOND WITHOUT CROSSING THRESHOLD OR
0224   *           FIRST TIME IN AFTER TURN ON
0225   *
0226   *
0227   *
0228   *
0229   TOUT  LDA TMOUT
0230         STA BCNTR     RESET TIME-OUT
0234   *
0235         LDA MIN0
0236         STA SMAX      SET TO ENSURE
0237         LDA MAX0      THAT A BEAT
0238         STA DMIN      WILL BE FOUND NEXT TIME
0239   *
0240         LDA PDATA     CURRENT VALUE
0241         STA BMAVG     SET STATUS VALUES
0242         STA FDAVG
0243         STA FSAVG
0244   *
0247   *               SYSTOLIC OR DIASTOLIC SEARCH.
0248   *
0249   S/D?  LDA PDATA
0250         ADB BMAVG
0251         JSB CMPAB               A CONTAINS PDATA
0252         JMP SYSTS     ABOVE THRESHOLD
0253         JMP DIASS     BELOW TH   A<B
0254   *                      TH IS BMAVG + OFSET
0257   *                   NEW DATA VALUE IS IN "A" REG (PDATA)
0258   *
0259   SYSTS LDB SMAX      PREVIOUS MAX       JMP L*-*N
0260         CPB MIN0
0261         JMP FTSYS     FIRST TIME IN?
0262   *
0263         JSB CMPAB             NEW MAX?
0264   *
0265         STA SMAX      NEW MAX
0266         JMP GREAN
```

```
0267           NEO              PROCESSING OF NEW DIASTOLIC VALUES
0268    *      FIRST TIME ON SYSTOLIC SIDE OF FENCE
0269    *      CALL THIS THE START OF A NEW BEAT
0270    *
0271    *
0272    FTSYS EQU *              FIRST TIME SYSTOLIC
0273    *
0274    *      SET SYSTOLIC TO CURRENT VALUE
0275           STA SMAX
0276    *
0277           LDB CMIN
0278           CPB MAX0         IF TIMEOUT
0279           STA DMIN              USE CURRENT VALUE FOR DIAST
0280    *
0281    *
0311    *
0312    *      UPDATE FAST AVERAGE
0313    *
0314    *
0315    *      THIS ROUTINE UPDATES A RUNNING AVERAGE BY THE METHOD
0316    *
0317    *      RAVG = (1.0 - FACTOR) * RAVG + FACTOR * NEWVAL
0318    *
0319    *      (RAVG = RAVG + FACTOR *(NEWVAL - RAVG)
0320    *
0321    *      THIS HAS AN EXPONENTIAL TIME RESPONSE SIMILAR TO AN R*C FILTER
0322    *
0323    *
0324    *      USE FACTOR = 1/2    GIVES TIME CONSTANT OF 2 BEATS
0325    *
0326    *      AND SIMPLIFY TO    RAVG= (RAVG+NEWVAL) / 2
0327    *
0328           LDB FDAVG
0329           ADB DMIN     -DIAST
0330           CLE,ERB      DIV BY 2 ASSUME DATA IS POSITIVE
0331           STB FDAVG
0332    *

0437    *
0458    *
0459    *          REDEFINE OFFSET
0500    *          USE CURRENT MINIMUM AS BEAT DIASTOLIC
0501    *          RESET FOR NEXT TIME
0502    *
0503    *
0504    DOFST  LDB FDAVG        FAST DIAST AVG
0505           CMB,INB          - DIAST
0506           ADB DMAVG        -MEAN-DIAST
0507           BRS,BRS          DIVIDE BY 4
0508           CMB,INB
0509           SSB,NSS
0510           CLB              NOT > 0
0511           STB OFSET        (DIAST-MEAN) / 4
0512    *
0513    *      RESET TIME OUT
0514    *
0515           LDB TMOUT
0516           STB BCNTR
0517    *
0518    *      SET MIN FOR NEXT TIME
0519    *
0520           LDA MAX0
0521           STA DMIN
0522           JMP GMEAN
0523           NEO              NEXT DIASTOLIC VALUE SEARCH
0524    *
0525    *
0526    DIASS  LDB DMIN
0527           CPM MAX0         FIRST TIME?
0528           JMP FTDIA        YES!
0529    *
0530           JSB CMPAB        NEW DIA?
0531    *
0532           JMP GMEAN        NO
0533    *
0534           STA DMIN         YES
0535           JMP GMEAN
0536    *
0537    *
0538           NEO              PROCESSING OF NEW SYSTOLIC VALUES
0539    *      FIRST TIME INTO DIASTOLIC REGION
0540    *          TAKE PREVIOUS MAX AS SYSTOLIC FOR THIS BEAT
0541    *          RESET OFFSET
0542    *          RESET FOR NEXT TIME
0543    *
0544    *
0545    *
0546    *
0547    FTDIA  EQU *            FIRST TIME DIASTOLIC
0548    *
0549    *      SET DIASTOLIC TO CURRENT VALUE
0550           STA DMIN
```

```
0551
0552         LDB SMAX
0553         CPB MIAN        IF TIME-OUT
0554         STA SMAX        USE CURRENT VALUE FOR SYST
0555
0556
0567    *    UPDATE FAST AVERAGE
0568
0569    *
0590    *    THIS ROUTINE UPDATES A RUNNING AVERAGE BY THE METHOD
0591
0592    *    RAVG = (1.0 - FACTOR) * RAVG + FACTOR * NEWVAL
0593
0594    *    (RAVG = RAVG + FACTOR *(NEWVAL - RAVG)
0595
0596    *    THIS HAS AN EXPONENTIAL TIME RESPONSE SIMILAR TO AN R-C FILTER
0597
0598
0599    *    USE FACTOR = 1/2      GIVES TIME CONSTANT OF 2 BEATS
0600
0601    *    AND SIMPLIFY TO    RAVG=(RAVG+NEWVAL) / 2
0602
0603         LDB FSAVG
0604         ADB SMAX        SYST
0605         CLE,ERB         DIV BY 2 ASSUME DATA IS POSITIVE
0606         STB FSAVG 0771
0772
0773    *    REDEFINE OFFSET
0774    *      USE CURRENT MAXIMUM AS BEAT SYSTOLIC
0775    *      RESET FOR NEXT TIME
0776
0777
0778  SGFST  LDE BRAVG       BEAT MEAN AVG
0779         CMB,INB         -MEAN
0780         ADB FSAVG       SYST-MEAN
0781         BRS             DIVIDE BY 2
0782         SSB
0783         CLB             NOT < 0
0784         STB OFSET       THRESHOLD MIDWAY BETWEEN MEAN AND SYST
0785
0786
0787    *    RESET TIME OUT
0788
0789         LDA TROUT
0790         STA BCNTR
0791
0792    *    SET MAX FOR NEXT TIME
0793
0794         LDA MINB
0795         STA SMAX
0796
0797         REB             -BEAT TO BEAT MEAN CALCULATION
0798    *    THIS ROUTINE UPDATES A RUNNING AVERAGE BY THE METHOD
0799
0800    *
0801
0802    *    RAVG = (1.0 - FACTOR) * RAVG + FACTOR * NEWVAL
0803
0804    *    (RAVG = RAVG + FACTOR *(NEWVAL - RAVG).
0805
0806    *    USE FACTOR = 1/16  GIVES TIME CONSTANT OF 20 SAMPLES
0807    *            20 * 20 MSEC = 0.4 SEC
0808
0809  BREAB  LDA BRAVG       OLD AVG
0810         CMA,INA
0811         ADA PDATA       NEW VALUE
0812         ARS,ARS
0813         ARS,ARS         DIVIDE BY 16
0814
0815         SSA,RSS         DITHER FOR VALUES BETWEEN 0 AND 16
0816         INA
0817
0818         ADA BRAVG
0819         STA BRAVG
0820
0821         JMP NEXT        NEXT DATA VALUE
0822         SPC 4
0823
0824
0825  MINB   DEC -32768
0826  MAXB   DEC  32767
0827  TROUT  DEC -250        SET FOR 5 SECONDS AT 50 HZ
0828
0829
0830
0831
0832
0833    *    REB CMPAR ROUTINE
0834
0835
0836
0837
```

```
8838  *    THIS ROUTINE RETURNS TO P+1 IF A = OR > B
8839  *    THIS ROUTINE RETURNS TO P+2 IF A < B
8840  *
8841  CMPAB NOP
8842        CMD,INB      .NOTE:
8843        ADS A        E AND C REGISTERS LOST!
8844        CMD,ISB,INB,RSS
8845        ISZ CMPAB
8846        ADS A
8847        JMP CMPAB,I
8848  *
8849        END
```

What is claimed is:

1. Apparatus for identifying the occurrence of cycles of dominant amplitudes in an information signal which may also contain other variations in amplitude wherein the cycles may have different durations, comprising
an input terminal to which an information signal may be applied,
filtering means for deriving at its output a filtered signal representing an average value of an information signal applied to said input terminal,
adding means for producing a reference signal at its output, said adding means having first and second inputs, said first input being coupled to the output of said filtering means,
comparing means having first and second inputs and an output, said first input being coupled to said input terminal so as to receive an information signal when present thereat, said second input being coupled to receive the reference signal at the output of said adding means, said comparing means producing at its output a control signal having a first value while the values of the signal at the first input of the comparing means is greater than the value represented by the signal applied to its second input and having a second value while the value of the signal applied to the first input of the comparing means is less than the value represented by the signal applied to its second input, and
offset deriving means responsive to said control signal for applying an offset value to the second input of said adding means of such polarity as to cause the value of the reference signal at the output of said adding means to shift to a value having a polarity with respect to the average value provided by said filtering means that is opposite to the polarity of a signal at said input terminal with respect to the references value.

2. In combination with apparatus as set forth in claim 1,
maximum value detecting means
control means responsive to said control signal for enabling said maximum value detecting means to detect the maximum value of signals derived from said input terminal at least during the portion of a cycle when said control signal has said first value,
means responsive to said control signal for resetting said maximum value detecting means once each cycle,
minimum value detecting means,
control means responsive to said control signal for enabling said minimum value detecting means to detect the minimum value of signals derived from said input at least during the portion of a cycle when said control signal has said second value, and
means responsive to said control signal for resetting said minimum value detecting means once each cycle.

3. Apparatus as set forth in claim 1 wherein said filtering means is adapted to provide a weighted average.

4. Apparatus as set forth in claim 2 wherein said offset driving means is comprised of means for deriving an average signal representing an average of the values represented by signals provided by one of said detecting means and means for deriving an offset signal representing at least a portion of the difference between the value represented by said average signal and the value represented by the filtered signal provided by said filtering means.

5. Apparatus as set forth in claim 4 wherein said means for deriving an average signal representing an average functions to provide a weighted average.

6. Apparatus as set forth in claim 4 further comprising means for initializing the apparatus comprising means for establishing the initial value of the signal at the output of said filtering means and the initial value of the signal at the output of the means for deriving the average signal at given values.

7. Apparatus as set forth in claim 6 further comprising means for activating said means for initializing the apparatus whenever the interval between successive changes of values of the control signal exceeds a given time.

8. Apparatus as set forth in claim 1 further comprising a pulse rate counter connected to receive said control signal.

9. Apparatus as set forth in claim 1 wherein said offset deriving means provides an offset having zero value while the output of said comparing means has a said first value.

10. Apparatus as set forth in claim 1 wherein said offset deriving means provides offsets having fixed values.

11. Apparatus for deriving a value representing at least one of the systolic and diastolic blood pressure values for a single heartbeat, comprising
an input,
means for applying values representing the variations of blood pressure with time to said input,
means for deriving an average value representing an average of the blood pressure represented by the values applied to said input,
means providing an offset value,
means for combining said offset value with the average value to provide a reference value,
peak value detecting means for detecting at least one of the systolic and diastolic blood pressures represented by values at said input, and
means for causing said peak detecting means to detect a peak value occurring while the values representing blood pressures at said input extend in the same direction with respect to said reference value as said average value.

12. Apparatus as set forth in claim 11 wherein said means for providing an offset value is coupled to the output of said peak value detecting means so as to derive an offset value that represents a function of the difference between an average of the values supplied by said peak value detecting means and said value representing an average of the blood pressure represented by the values applied to said input.

13. The method of deriving a value representing one of the systolic and diastolic blood pressures from values representing the variation of blood pressure with time, comprising deriving an average of the values representing the variation in blood pressure with time, combining an offset with average value to form a reference value, detecting peak values derived from the values representing the variation with time of the blood pressure that extend in the same direction from the reference value as the average value, and means for adjusting the value of said offset to be a function of the difference between an average of the values supplied by said peak value detecting means and said value representing said average of the variation of blood pressure with time.

14. Apparatus for identifying cycles of a signal and for deriving desired peak values of the signal of one polarity, the signal including desired dominant peak values and undesired peak values, comprising an input terminal to which the signal may be applied, averaging means coupled to said input for deriving at an output thereof an average value of the signal, adding means having first and second inputs and an ouput, means coupling said first input of said adding means to receive the output of said averaging means, means for comparing a signal at said input terminal with the output of said adding means so as to produce a first indication while a signal at said input terminal has said one polarity with respect to the output of said adding means and a second indication while a signal at said input terminal has the opposite polarity with respect to the output of said adder, successive ones of said first and second indications defining a cycle, means responsive to said first indication for deriving during the time said first indication is present a signal value corresponding to the greatest peak value of said one polarity of signals present at said input terminal, means responsive to said second indication for deriving during the time said second indication is present a signal value corresponding to the greatest peak value of said opposite polarity of signals present at said input terminal, means for producing a signal representing an average of peak values derived by said latter mans during previous second indications, means coupled to said latter means for deriving an offset value that is a given portion of the difference between the average of peak values derived by said latter means and the said average value of the signal produced by said averaging means, and means coupled to said means for deriving an offset value for applying the offset value to the second input of said adding means during said second indication with such polarity as to cause the output of said adding means to shift toward the said one polarity, whereby undesired peaks of said one polarity have to have a greater amplitude in order to change the output of said comparing means from the first indication to the second.

* * * * *

UNITED STATES PATENT AND TRADEMARK OFFICE
CERTIFICATE OF CORRECTION

PATENT NO. : 4,223,682
DATED : September 23, 1980
INVENTOR(S) : Allan P. Sherman It is certified that error appears in the above-identified patent and that said Letters Patent are hereby corrected as shown below:

| | | |
|---|---|---|
| Column 1 | line 17 | "evaluations" should read -- relaxations -- |
| Column 2 | line 62 | before "$O_{D2}$", insert -- $O_{S2}$ -- |
| Column 7 | line 49 | "vlaue" should read -- value -- |
| Column 13 | line 10 | "ofthe" should read -- of the -- |
| | line 50 | "corssings" should read -- crossings -- |
| Column 14 | line 35 | "BAMVG" should read -- BMAVG -- |
| Column 21 | line 50 | "references should read -- reference -- |

Signed and Sealed this

Tenth Day of February 1981

[SEAL]

Attest:

RENE D. TEGTMEYER

Attesting Officer

Acting Commissioner of Patents and Trademarks